United States Patent
Chang et al.

(10) Patent No.: US 9,360,303 B2
(45) Date of Patent: Jun. 7, 2016

(54) HEIGHT MEASURING APPARATUS AND METHOD THEREOF

(71) Applicant: Wistron Corp., New Taipei (TW)

(72) Inventors: Yao-Tsung Chang, New Taipei (TW); Chia-Hsien Li, New Taipei (TW); Pai-Yang Lin, New Taipei (TW); Shun-Chi Chung, New Taipei (TW)

(73) Assignee: WISTRON CORP., New Taipei (TW)

( * ) Notice: Subject to any disclaimer, the term of this patent is extended or adjusted under 35 U.S.C. 154(b) by 0 days.

(21) Appl. No.: 14/275,516

(22) Filed: May 12, 2014

(65) Prior Publication Data

US 2015/0176975 A1 Jun. 25, 2015

(30) Foreign Application Priority Data

Dec. 20, 2013 (TW) .............................. 102147475 A (51) Int. Cl.
*G01C 3/08* (2006.01)
*G01B 11/06* (2006.01)
*A61B 5/107* (2006.01)

(52) U.S. Cl.
CPC .......... *G01B 11/0608* (2013.01); *A61B 5/1072* (2013.01); *A61B 2562/0233* (2013.01)

(58) Field of Classification Search
CPC ................................. G01C 3/08; G01S 15/002
See application file for complete search history.

(56) References Cited

U.S. PATENT DOCUMENTS

| 5,337,137 A * | 8/1994 | Ogawa et al. ................. 356/4.07 |
| 5,661,561 A * | 8/1997 | Wurz ................... G01B 11/0608 250/223 R |
| 6,075,605 A * | 6/2000 | Futamura et al. ............. 356/608 |
| 6,246,482 B1 * | 6/2001 | Kinrot ....................... G01D 5/26 356/499 |
| 2005/0237511 A1* | 10/2005 | Takahashi et al. ............ 356/121 |
| 2010/0188336 A1* | 7/2010 | Ng ......................... G06F 1/1616 345/163 |
| 2010/0246898 A1 | 9/2010 | Izumi |
| 2010/0298708 A1* | 11/2010 | Pan .............................. 600/449 |

OTHER PUBLICATIONS

TW Office Action dated Aug. 26, 2015 in application No. 102147475.
TW Office Action dated Feb. 2, 2016 in application No. 102147475.

* cited by examiner

*Primary Examiner* — Luke Ratcliffe
*Assistant Examiner* — Samantha K Abraham
(74) *Attorney, Agent, or Firm* — Maschoff Brennan (57) ABSTRACT

A height measuring apparatus and a method thereof are disclosed. The disclosed method is suitable for an indoor environment. The disclosed method comprises emitting a first laser to a ceil via a first light path, determining whether a first reflective light corresponding to the first laser is received, emitting a second laser to an object via a second light path reflected by the ceil, determining whether a second reflective light corresponding to the second laser is received, calculating a first length according to a first data corresponding to the first reflective light, calculating a second length according to a second data corresponding to the second reflective light, and calculating an object height of the object according to the first length and the second length.

22 Claims, 13 Drawing Sheets

HEIGHT MEASURING APPARATUS AND METHOD THEREOF

CROSS REFERENCE

The present application is based on, and claims priority from, Taiwan Application Serial Number 102,147,475, filed on Dec. 20, 2013, the disclosure of which is hereby incorporated by reference herein in its entirety.

TECHNIQUE

1. Field

The present invention generally relates to a height measuring apparatus and a method thereof, and more particularly, to a height measuring apparatus utilizing a laser ranging method and the method thereof.

2. Background

Conventionally, the height measuring apparatus has to be integrated into the scale for measuring the height and the weight of one user at the same time. The conventional scale integrated with the height measuring apparatus usually occupies large space and is not easy to be carried by the user. Moreover, to operate the scale, an assistant is needed to help the user measure his/her height.

SUMMARY OF THIS INVENTION

A method for measuring height according to one or more exemplary embodiments of this invention is applicable for an environment with a reflecting surface. The method comprises: emitting a first laser beam along a first light path, determining whether a first reflecting light resulting from the first laser beam reflected by the first reflecting surface is received, calculating a first length according to a first piece of data corresponding to the first reflecting light when the first reflecting light is received, emitting a second laser beam along a second light path, determining whether a second reflecting light resulting from the second laser beam reflected by both of the first reflecting surface and an object under test is received, calculating a second length according to a second piece of data corresponding to the second reflecting light when the second reflecting light is received, and calculating a height of the object under test at least according to the first length and the second length.

A height measuring apparatus according to one or more exemplary embodiments of this invention is applicable for an environment with a reflecting surface. The apparatus comprises a baseboard, at least one laser beam emitting module, at least one photo detection module, and a control module. The baseboard has a top surface for carrying an object under test. The at least one laser beam emitting module is disposed in at least one emitting position on the top surface of the baseboard. The at least one laser beam emitting module is used for emitting a first laser beam along a first light path and emitting a second laser beam along a second light path. The at least one photo detection module is disposed in at least one detecting position on the top surface of the baseboard. The at least one photo detection module is used for selectively generating a first piece of data corresponding to a first reflecting light and a second piece of data corresponding to a second reflecting light by determining whether the first reflecting light resulting from the first laser beam reflected by the first reflecting surface and the second reflecting light resulting from the second laser beam reflected by both of the object under test and the first reflecting surface. The control module is electrically coupled to the laser beam emitting module and the photo detection module. The control module is used for calculating a first length according to the first piece of data, calculating a second length according to the second piece of data, and calculating a height of the object under test at least according to the first length and the second length.

In order to make the aforementioned and other features of the present invention more comprehensible, several embodiments accompanied with figures are described in detail below.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THIS INVENTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1A:
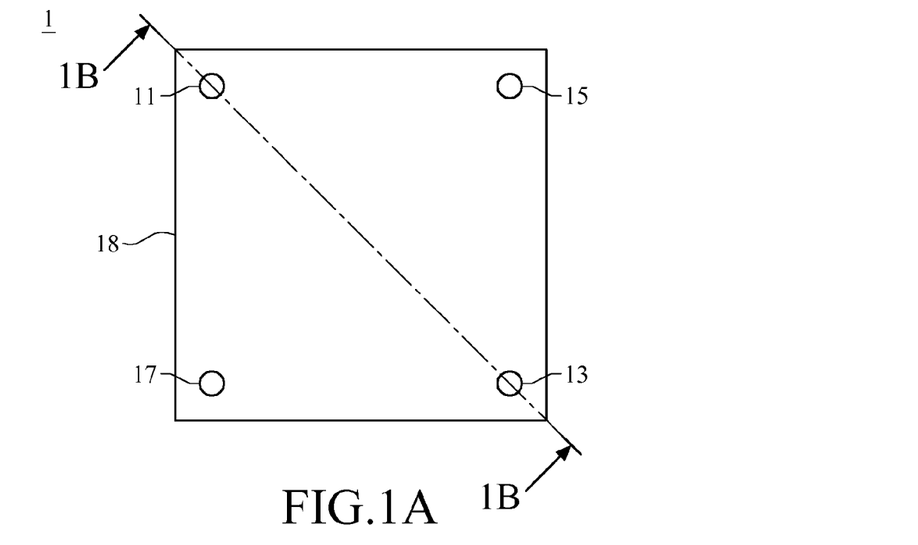
FIG. 1A is a top view of a height measuring apparatus according to one embodiment of this invention.
Figure 1B:
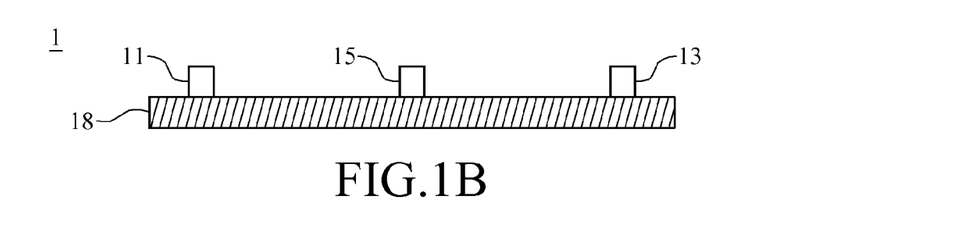
FIG. 1B is a cross-section view corresponding to FIG. 1A.
Figure 1C:
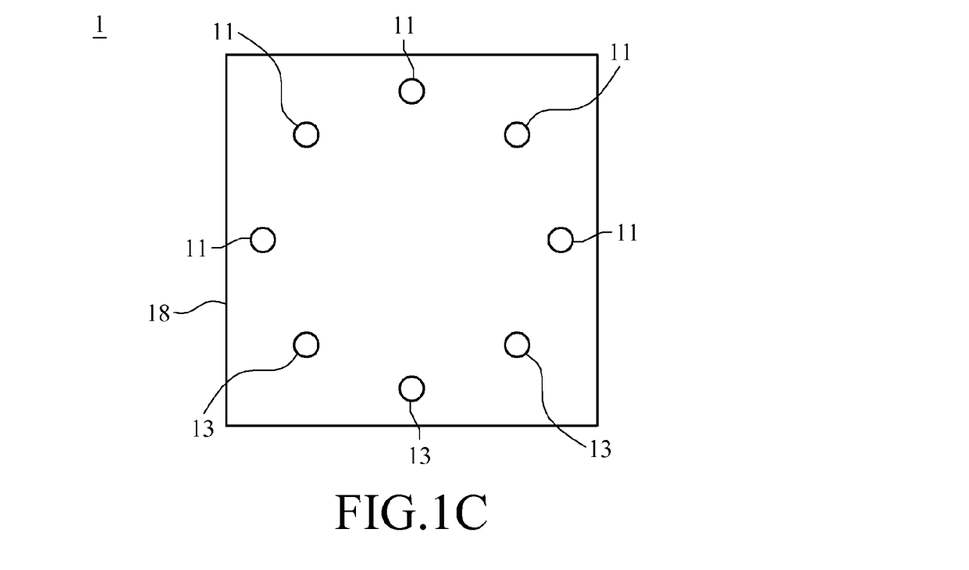
FIG. 1C is a top view of a height measuring apparatus according to another embodiment of this invention.

Please refer to FIG. 1A and FIG. 1B for understanding a height measuring apparatus according to one embodiment of this invention, wherein FIG. 1A is a top view of a height measuring apparatus according to one embodiment of this invention, while FIG. 1B is a cross-section view corresponding to FIG. 1A. As shown in FIG. 1A, a height measuring apparatus 1 may comprise a first laser beam emitting module 11, a first photo detection module 13, a second laser beam emitting module 15, a second photo detection module 17, and a baseboard 18. The first laser beam emitting module 11 and the second laser beam emitting module 15 are respectively disposed in a first emitting position and a second emitting position on the top surface of the baseboard 18, while the first photo detection module 13 and the second photo detection module 17 are respectively disposed in a first detecting position and a second detecting position on the top surface of the baseboard 18. In another embodiment, please refer to FIG. 1C, which is a top view of a height measuring apparatus according to one embodiment of this invention. As shown in FIG. 1C, the height measuring apparatus 1 may comprise a plurality of first laser beam emitting module 11, a plurality of first photo detection module 13, and the baseboard 18.

Figure 2:
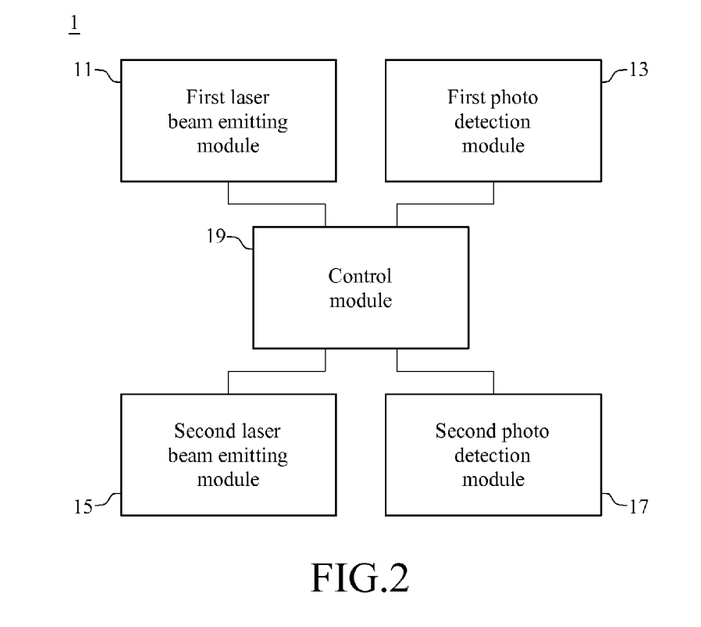
FIG. 2 is a functional block diagram of the height measuring apparatus according to one embodiment of this invention.

As to the height measuring apparatus 1 shown in FIG. 1A, please refer to FIG. 2, which is a functional block diagram of the height measuring apparatus according to one embodiment of this invention. As shown in FIG. 2, the height measuring apparatus 1 may comprise a first laser beam emitting module 11, a first photo detection module 13, a second laser beam emitting module 15, a second photo detection module 17, and a control module 19, which is not illustrated in FIG. 1A but in FIG. 2. The control module 19 is electrically coupled to the first laser beam emitting module 11, the first photo detection module 13, the second laser beam emitting module 15, and the second photo detection module 17, respectively.

However, in another embodiment, the height measuring apparatus 1 may comprise neither the second laser beam emitting module 15 nor the second photo detection module 17. In this embodiment, the control module 19 is electrically coupled to the first laser beam emitting module 11 and the first photo detection module 13.

In one embodiment related to FIG. 2, the control module 19 may control the first laser beam emitting module 11 to emit a first laser beam along a first light path and control the second laser beam emitting module 15 to emit a second laser beam along a second light path. Take the first light path for example, the first light path is corresponding to the first emitting position of the first laser beam emitting module 11 and a first emitting angle, so the first light path may be adjusted by changing, modifying, or adjusting the first emitting position, such as moving the first laser beam emitting module 11 to another position or choosing another first laser beam emitting module, and/or the first emitting angle. According to the same or similar method, the second light path may be adjusted. According to this invention, the laser beam emitting module aforementioned may be, for example but not limited to, a gas laser device, a chemical laser device, a excimer laser device, a solid-state laser device, a fiber laser device, a photonic crystal laser device, a semiconductor laser device, a dye laser device, a free-electron laser device, exotic media, or any other devices applicable for generating a laser beam.

In one embodiment corresponding to FIG. 2, it may be determined by the first photo detection module 13 whether a first reflecting light corresponding to the first laser beam is received by the first photo detection module 13, and the first photo detection module 13 may selectively and accordingly generate a first piece of data corresponding to the first reflecting light. With similar method, it may be determined by the second photo detection module 17 whether a second reflecting light corresponding to the second laser beam is received by the second photo detection module 17, and the second photo detection module 17 may selectively and accordingly generate a second piece of data corresponding to the second reflecting light.

Specifically, take the first photo detection module 13 for example. The first photo detection module 13 may comprise a charge-coupled device (CCD) and a comparator. When the CCD receives light with particular frequency/spectrum distribution, which is identical or similar to that of the first laser beam in this invention, the CCD generates a first coupling signal. The comparator compares the first coupling signal with a first intensity threshold. When the voltage and/or the current of the first coupling signal is greater than the first intensity threshold, the comparator determines that the first photo detection module 13 has receive the first reflecting light corresponding to the first laser beam. With the same method, the second photo detection module 17 may determine whether a second reflecting light corresponding to the second laser beam is received according to a second intensity threshold.

On the contrary, in another embodiment, the height measuring apparatus 1 has neither the second laser beam emitting module 15 nor the second photo detection module 17, so the control module 19 may control the first laser beam emitting module 11 to emit the first laser beam along the first light path and then emit the second laser beam along the second light path. Also, the control module 19 may control the first photo detection module 13 to determine whether the first reflecting light corresponding to the first laser beam and the second reflecting light corresponding to the second laser beam are both received so as to selectively generate the first piece of data corresponding to the first reflecting light and the second piece of data corresponding to the second reflecting light.

The control module 19 is used for calculating the first length according to the first piece of data, calculating the second length according to the second piece of data, and calculating the height of the object under test according to both of the first length and the second length. For example, the first piece of data may comprise the first emitting time at which the first laser beam is emitted and the first receiving time at which the first reflecting light is received, while the second piece of data may comprise the second emitting time at which the second laser beam is emitted and the second receiving time at which the second reflecting light is received.

Because the speed of light is constant, the first length may be calculated according to the first emitting time and the first receiving time, and the second length may be calculated according to the second emitting time and the second receiving time. In another embodiment, the first piece of data may comprise a first emitting phase of the first laser beam and a first receiving phase of the first reflecting light, while the second piece of data may comprise a second emitting phase of the second laser beam and a second receiving phase of the second reflecting light. These phases may be used for calculating the first length and the second length. After both of the first length and the second length are calculated, the height of the object under test may also be calculated according to both of the first length and the second length. According to this invention, the control module 19 may be realized with an application-specific integrated circuits (ASIC), an advanced RISC machine (ARM), a central processing unit (CPU), a mono-chip controller, or any other devices applicable for performing logic operation, arithmetic operation, and manipulation.

Figure 3A:
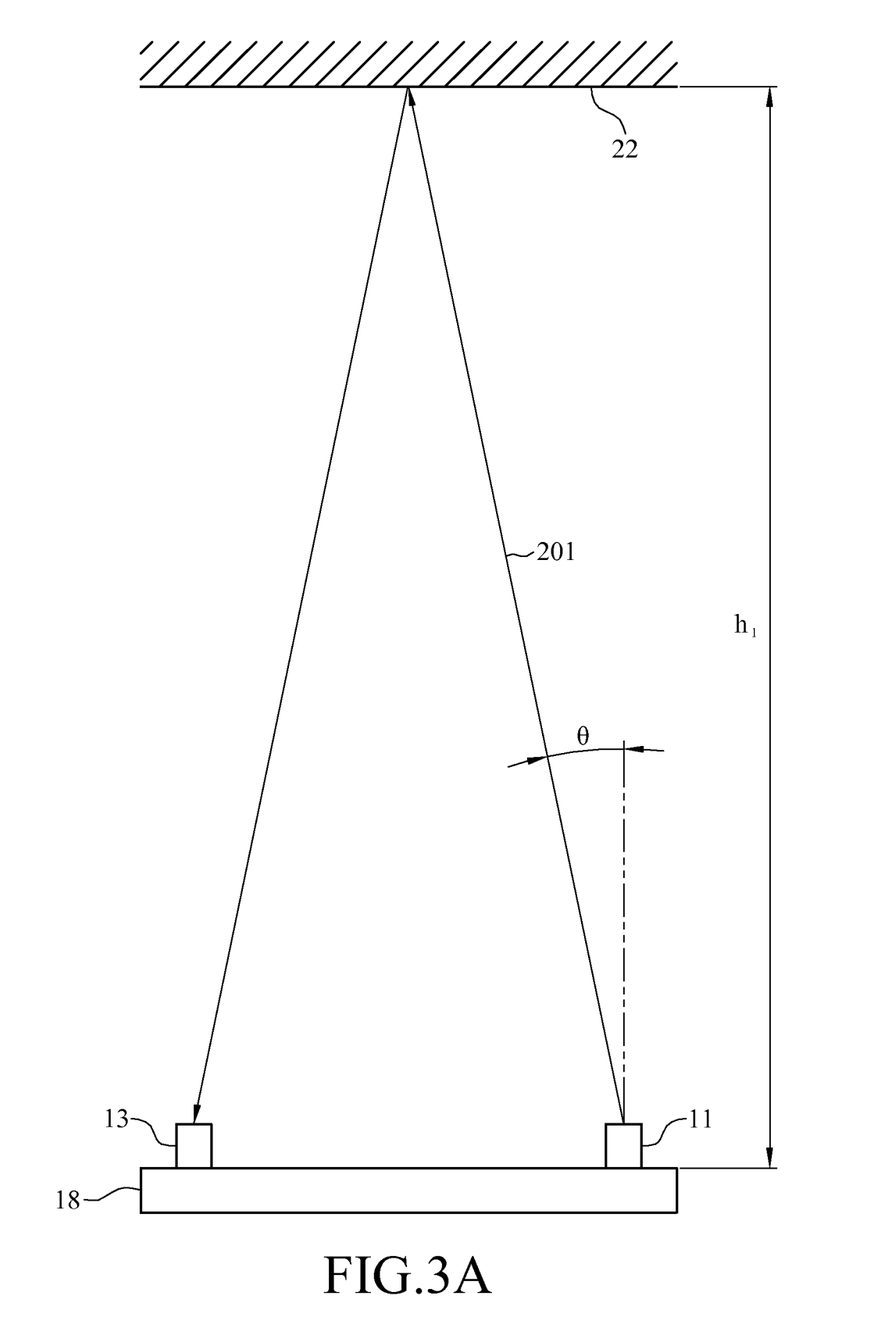
FIG. 3A illustrates a schematic view of the operation of the height measuring apparatus according to one embodiment of this invention.

Referring to the calculation of the height of the object under test, please refer to FIG. 2 in combination with FIG. 3A, which illustrates a schematic view of the operation of the height measuring apparatus according to one embodiment of this invention. As shown in FIG. 3A, the control module 19 controls the first laser beam emitting module 11 to emit the first laser beam to a reflecting surface 22, which is not necessarily a reflective surface, along the first light path 201. Specifically, when the object under test, a man, is standing, the reflecting surface 22 may be the ceiling of a room in a house. When the object under test, the man, is lying, the reflecting surface 22 may be a wall or a bezel.

Then, the first photo detection module 13 may determine whether the first reflecting light, which results from the first laser beam, reflected by the reflecting surface 22 and the control module 19 may accordingly calculate the first length h1, the distance between the baseboard 18 and the reflecting surface 22, with the aforementioned method. Specifically, the length of the first light path 201, starting from the baseboard 18 to the reflecting surface 22 and then going back to the baseboard 18, may be calculated according to the first emitting time and the first receiving time as aforementioned. When the first light path 201 is almost perpendicular, that is, an emitting angle θ, relative to a normal of the top surface of the baseboard 18, as shown in FIG. 3A is close to be zero, the length of the first light path, from the first laser beam emitting module 11 to the reflecting surface 22 and back to the photo detection module 13, may be roughly seen as twice as the first length h1. Otherwise, when the emitting angle θ as shown in FIG. 3A is too large to be neglect, the first length h1 can be calculated as half of the product of the length of the first light path 201 and cos(θ).

In one embodiment, the baseboard 18 may be settled inappropriately or the first light path 201 may be set with mistake, so the first photo detection module 13 can neither receive the first reflecting light corresponding to the first laser beam nor generate the first piece of data according to the first reflecting light. To avoid such circumstances, the control module 19 may further determine whether it, the control module 19, receives the first piece of data before a first timing threshold. If the first piece of data is not received before the first timing threshold, the control module 19 may alert the user or directly control the first laser beam emitting module 11 to adjust the first light path 201 to emit the first laser beam again. The method for adjusting the first light path is aforementioned.

Figure 3B:
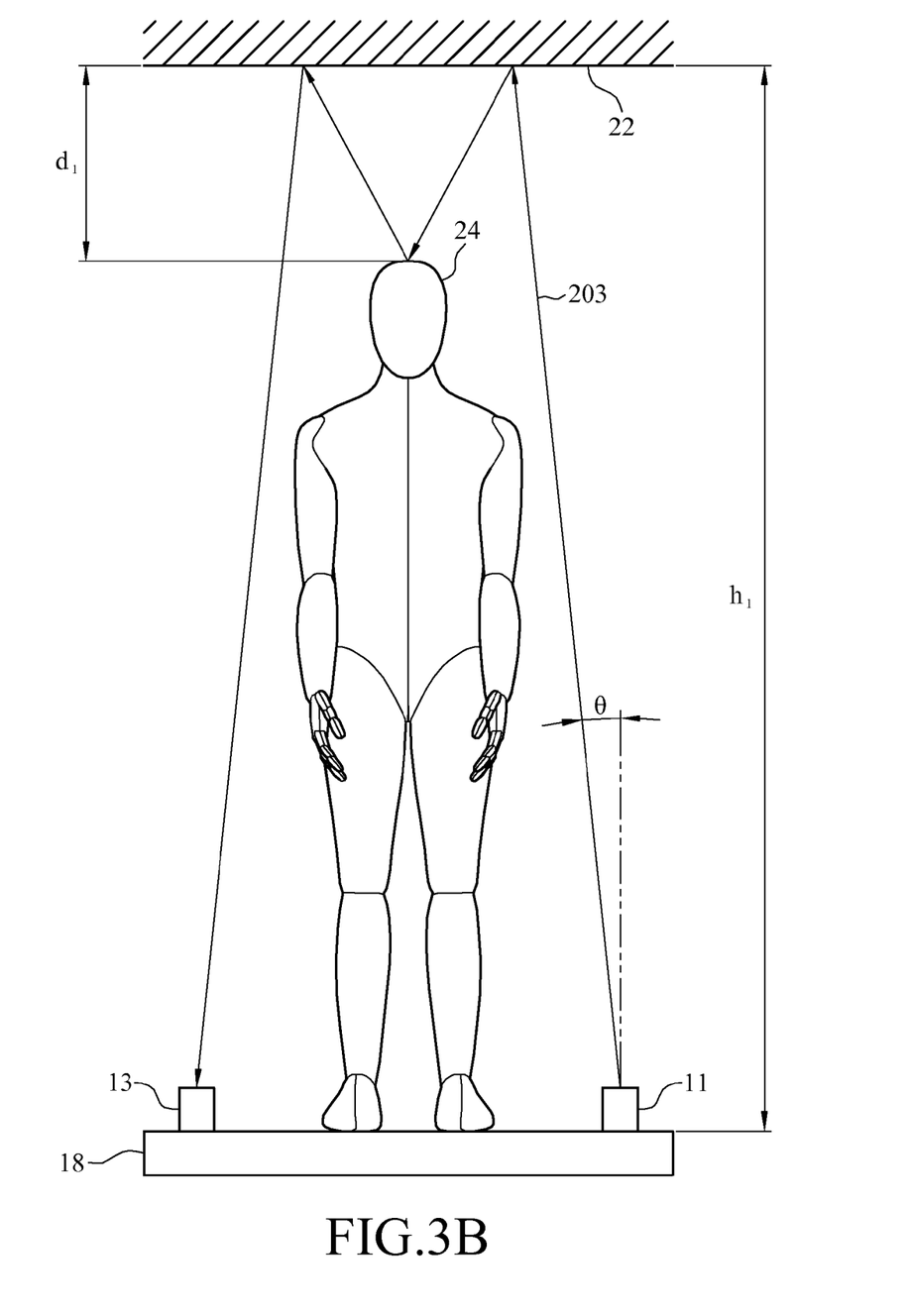
FIG. 3B illustrates a schematic view of the operation of the height measuring apparatus according to one embodiment of this invention.

Please now refer to FIG. 3B, which illustrates a schematic view of the operation of the height measuring apparatus according to one embodiment of this invention. As shown in FIG. 3B, when a user 24 stands on the baseboard 18, the control module 19 may control the first laser beam emitting module 11 to emit the second laser beam along the second light path 203, and then the first photo detection module 13 may detect the second reflecting light corresponding to the second laser beam. After the second reflecting light is detected, the length of the second light path 203 may be calculated and as a consequence a second length d1, which is the distance between the reflecting surface 22 and the top of the head of the user 24, may be calculated as well.

Explicitly, when the emitting angle θ is closed to be zero, the length of the second light path 203 may be seen as the summation of twice of the first length h1 and twice of the second length d1. When the emitting angle θ cannot be neglect, the product of the length of the second light path 203 and cos(θ) may be seen as the summation of twice of the first length h1 and twice of the second length d1. As such, the second length d1 may be calculated, and as well as the height of the object under test, how tall the user 24.

Figure 3C:
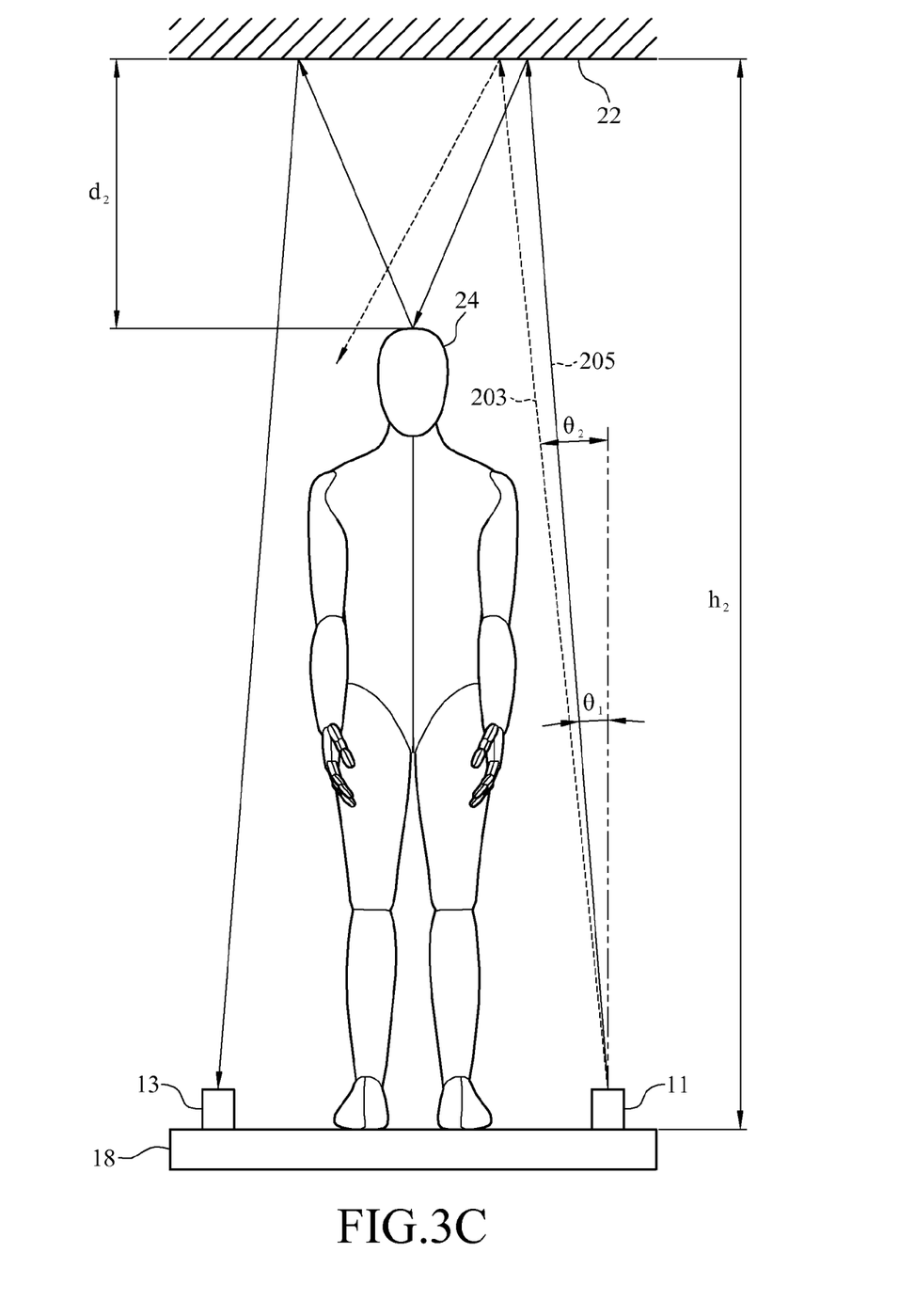
FIG. 3C is a schematic of the operation of the height measuring apparatus according to one embodiment of this invention.
Figure 3D:
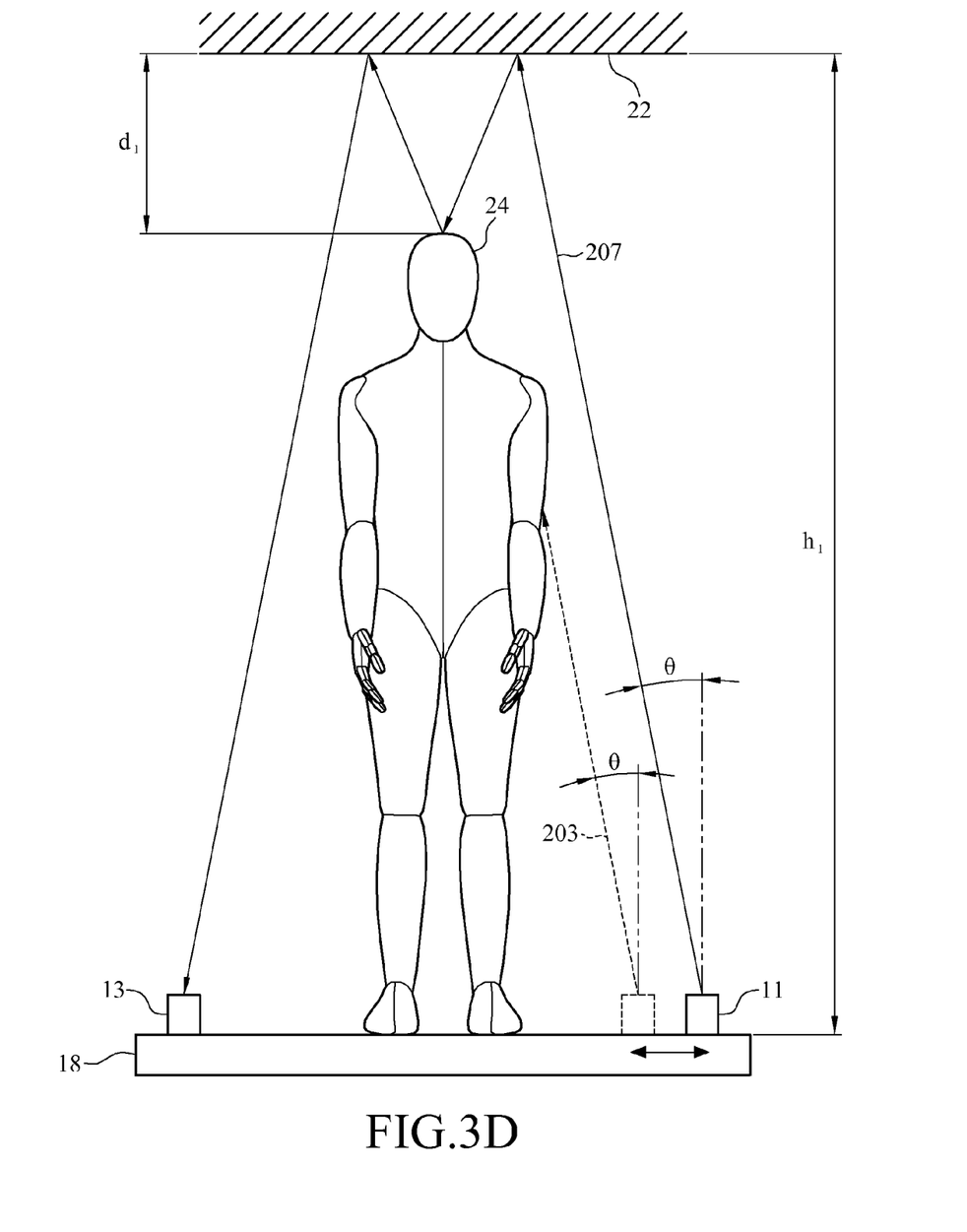
FIG. 3D is a schematic of the operation of the height measuring apparatus according to one embodiment of this invention.

In certain embodiments, please refer to FIG. 3C and FIG. 3D, wherein FIG. 3C and FIG. 3D are respectively a schematic view of the operation of the height measuring apparatus according to one embodiment of this invention. In FIG. 3C, the distance between the reflecting surface 22 and the baseboard 18, the height h2, is greater than the distance between the reflecting surface 22 and the baseboard 18 in FIG. 3B, the first length h1. Consequently, when the first laser beam emitting module 11 emits the second laser beam along the original second light path 203, the first photo detection module 13 cannot receive the second reflecting light corresponding to the second laser beam correctly. The second piece of data cannot be generated by the first photo detection module 13 according to the second reflecting light correspondingly. If the control module 19 determines that no second piece of data is received within/before the second timing threshold, such as one second after the second laser beam is emitted, the control module 19 may control the first laser beam emitting module 11 to adjust the emitting angle θ so as to adjust the second light path 203 to the adjusted second light path 205. The first laser beam emitting module 11 then emits the second laser beam along the adjusted second light path 205 again.

In FIG. 3D, the second laser beam emitted by the first laser beam emitting module 11 along the original second light path 203 is blocked by the user 24 and the second reflecting light cannot be received by the first photo detection module 13 correctly. Hence, the second piece of data cannot be generated by the first photo detection module 13 according to the second reflecting light. If the control module 19 determines that no second piece of data is received within/before the second timing threshold, such as one second after the second laser beam is emitted, the control module 19 may control the first laser beam emitting module 11 to adjust the emitting position so as to adjust the second light path 203 to the adjusted second light path 207. The first laser beam emitting module 11 then emits the second laser beam along the adjusted second light path 207 again.

Figure 3E:
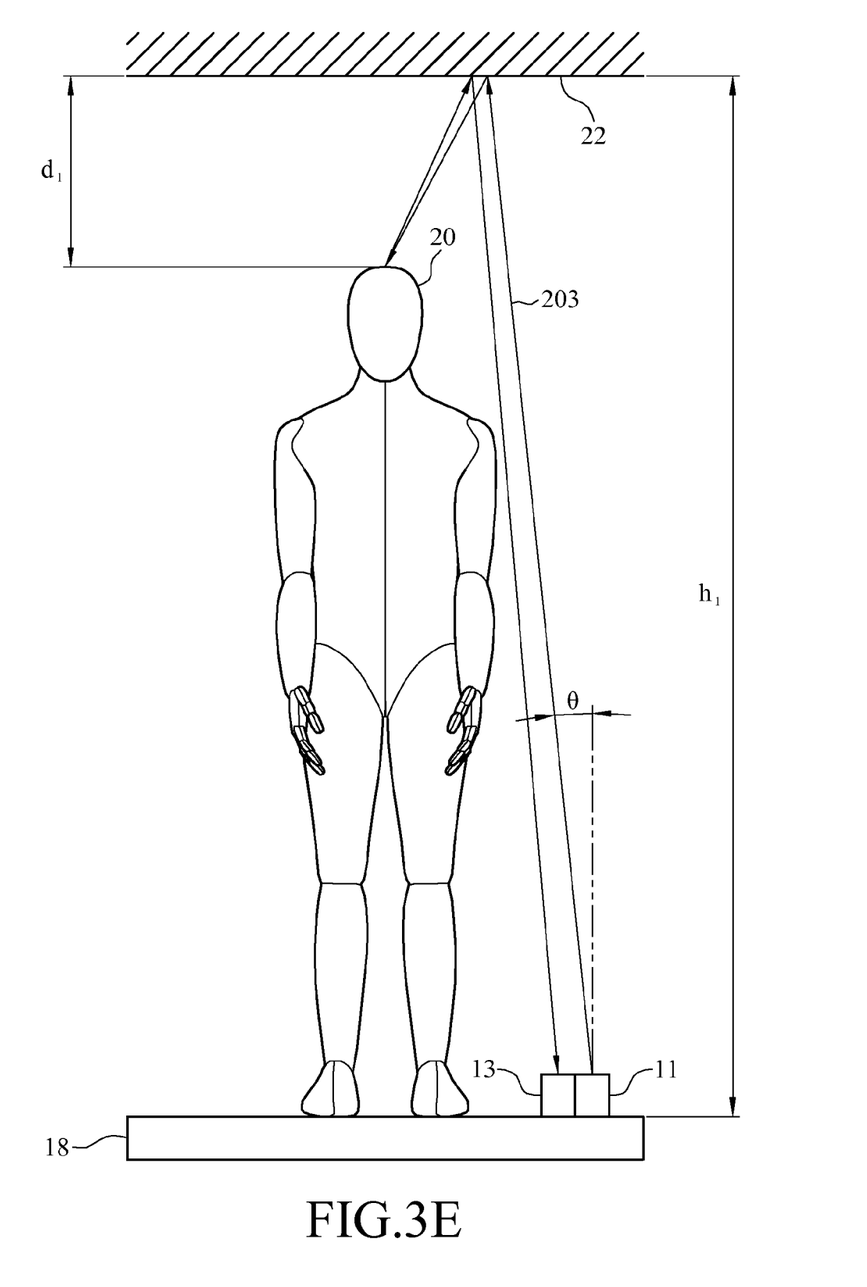
FIG. 3E illustrates a schematic view of the operation of the height measuring apparatus according to one embodiment of this invention.

In one embodiment, the first laser beam emitting module 11 and the first photo detection module 13 may be in the same or in adjacent position on the baseboard 18, as shown in FIG. 3E, which illustrates a schematic view of the operation of the height measuring apparatus according to one embodiment of this invention. As shown in FIG. 3E, the first laser beam emitting module 11 may emit the first laser beam and/or the second laser beam in the first emitting position and the photo detection module 13 may receive the first reflecting light and the second reflecting light respectively in the first emitting position, which is clearly also the first receiving position.

Figure 3F:
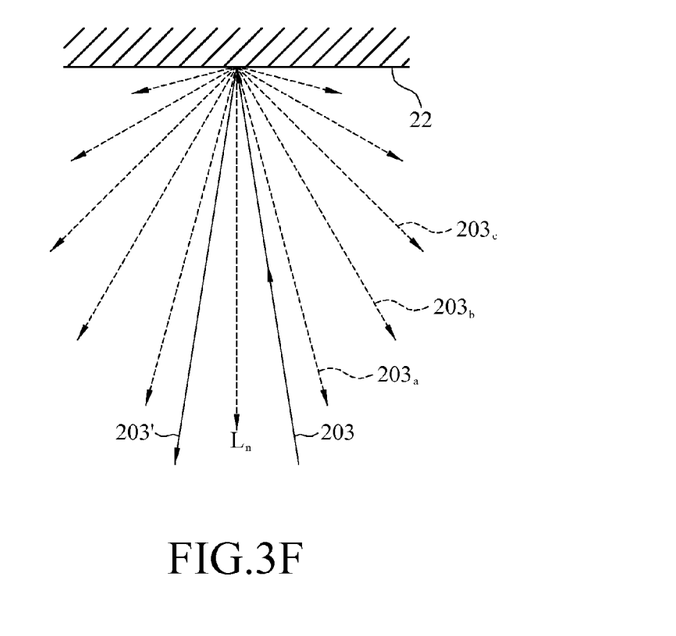
FIG. 3F is a schematic view for explaining the phenomenon in FIG. 3E with a Lambert radiator.

It may be doubted that the second light path 203 in FIG. 3E does not conform to the law of reflection. Please refer to FIG. 3F for understanding, wherein FIG. 3F is a schematic view for explaining the phenomenon in FIG. 3E with a Lambert radiator. In most embodiments, neither the reflecting surface 22 nor the top of the head of the user 20 is a perfect reflective surface. For example, the reflecting surface 22 may be seen as a reflecting surface whose property is partially the reflective surface and partially a Lambert radiator. Hence, as shown in FIG. 3F, while the incident light runs along the second light path 203 to the reflecting surface 22, there may be one primary reflecting light 203' and some secondary reflecting light 203a through 203c generated. More explicitly, the intensity of the primary reflecting light 203' and the intensity of each of the secondary reflecting light in combination is roughly equal to the intensity of the incident light from the second light path 203. Accordingly, the surface of the object under test needs not to be perpendicular to the laser beam while a laser ranging method is performed. As well, the first photo detection module 13 can detect the secondary reflecting light with certain intensity from an angle other than the reflective angle which is corresponding to the incident angle.

As a consequence, in one embodiment, the control module 19 may control the first laser beam emitting module 11 to emit laser beam once and control the first photo detection module 13 to detect the first reflecting light and the second reflecting light. In the present embodiment, the first reflecting light is resulting from the laser beam reflected by the reflecting surface 22, while the second reflecting light is resulting from the laser beam reflected by the reflecting surface 22 to the top of the head of the user 20, then back to the reflecting surface 22, and then reflected by the reflecting surface 22 again to the first photo detection module 13, as shown in FIG. 3E.

Figure 3G:
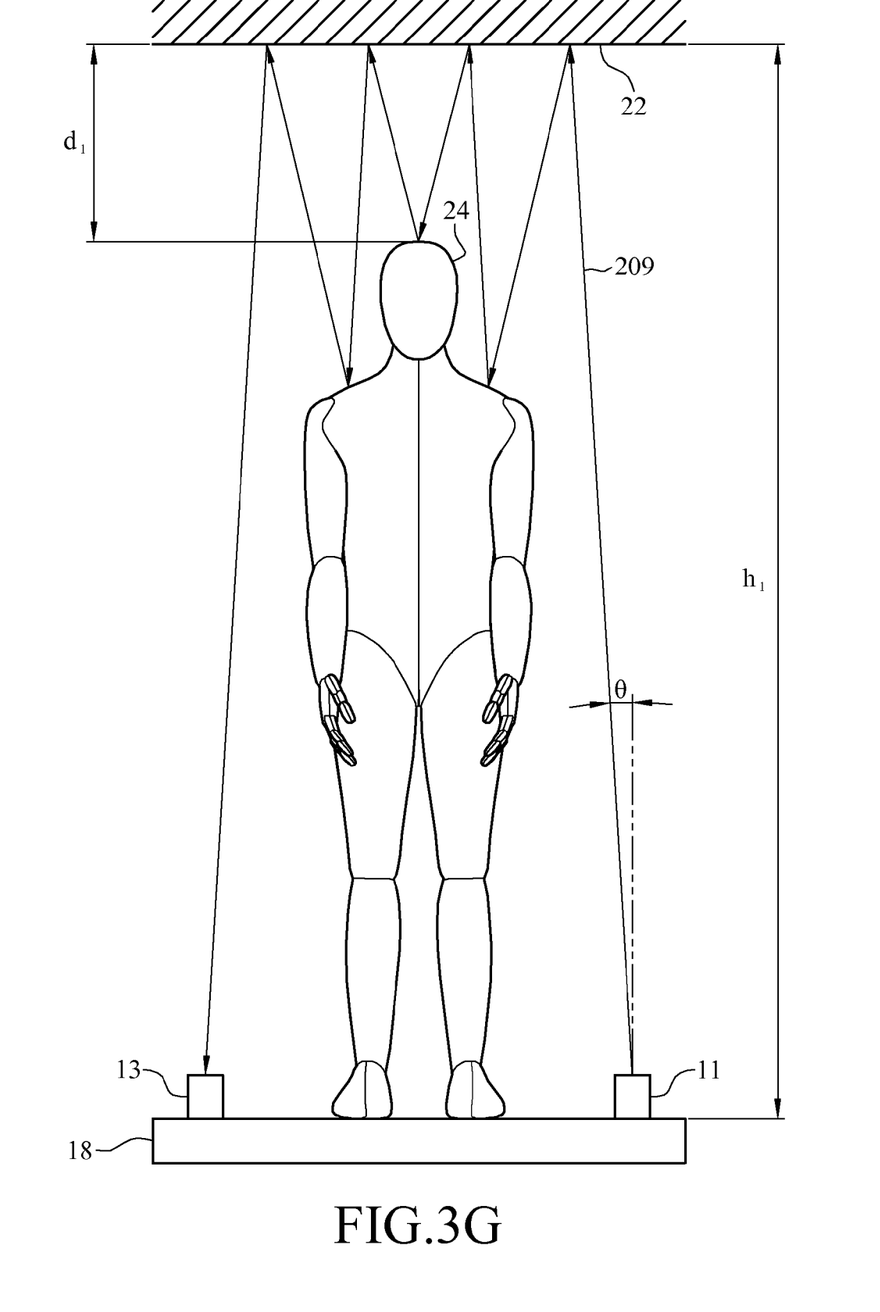
FIG. 3G illustrates a false operation of the height measuring apparatus according to one embodiment of this invention.

In one embodiment, please refer to FIG. 3G, which illustrates a false operation of the height measuring apparatus according to one embodiment of this invention. As shown in FIG. 3G, when the first laser beam emitting module 11 emits the laser beam along a light path 209, the first photo detection module 13 might detect a corresponding reflecting light. If the control module 19 takes the length of the light path 209 as the summation of twice of the first length h1 and twice of the second length d1, the result of the calculation, the height of the user 24, cannot be correct. As such, there is an error prevention mechanism needed by the height measuring apparatus.

Figure 4:
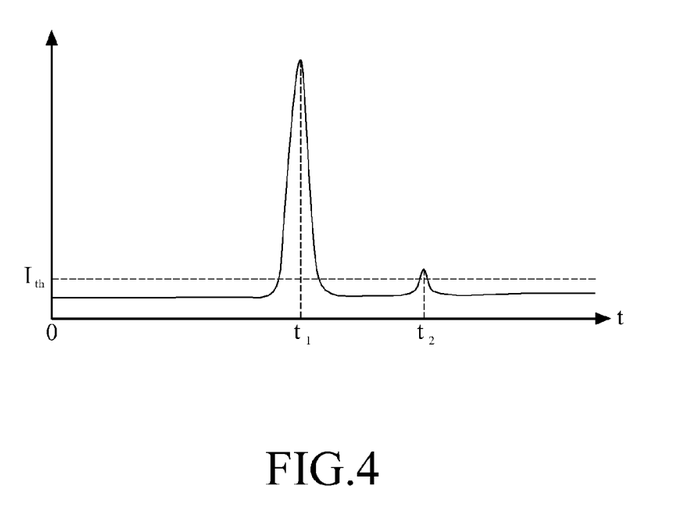
FIG. 4 is a diagram of a light intensity versus time according to one embodiment in this invention.

Please refer to FIG. 4, which is a diagram of a light intensity versus time according to one embodiment in this invention. The CCD in the first photo detection module 13 may continuously detect light with the same frequency as the emitted laser beam and the intensity of the outputted coupling signal is non-zero consequently. However, an intensity threshold Ith may be set, or a first intensity threshold and a second intensity threshold respectively correspond to the first reflecting light and the second reflecting light may be set. Hence, coupling signal with intensity lower than the intensity threshold may be filtered out. Take the laser beam along the light path 209 for example, the times of reflection of said laser beam is more than expected, such as twice, the intensity of the corresponding coupling signal is then lower than the intensity threshold Ith and is consequently ignored. Hence, as shown in FIG. 4, the first photo detection module 13 only recognizes the first reflecting light, received at time t1, and the second reflecting light, received at time t2, so the possibility of the occurrence of errors is reduced tremendously.

Figure 5A:
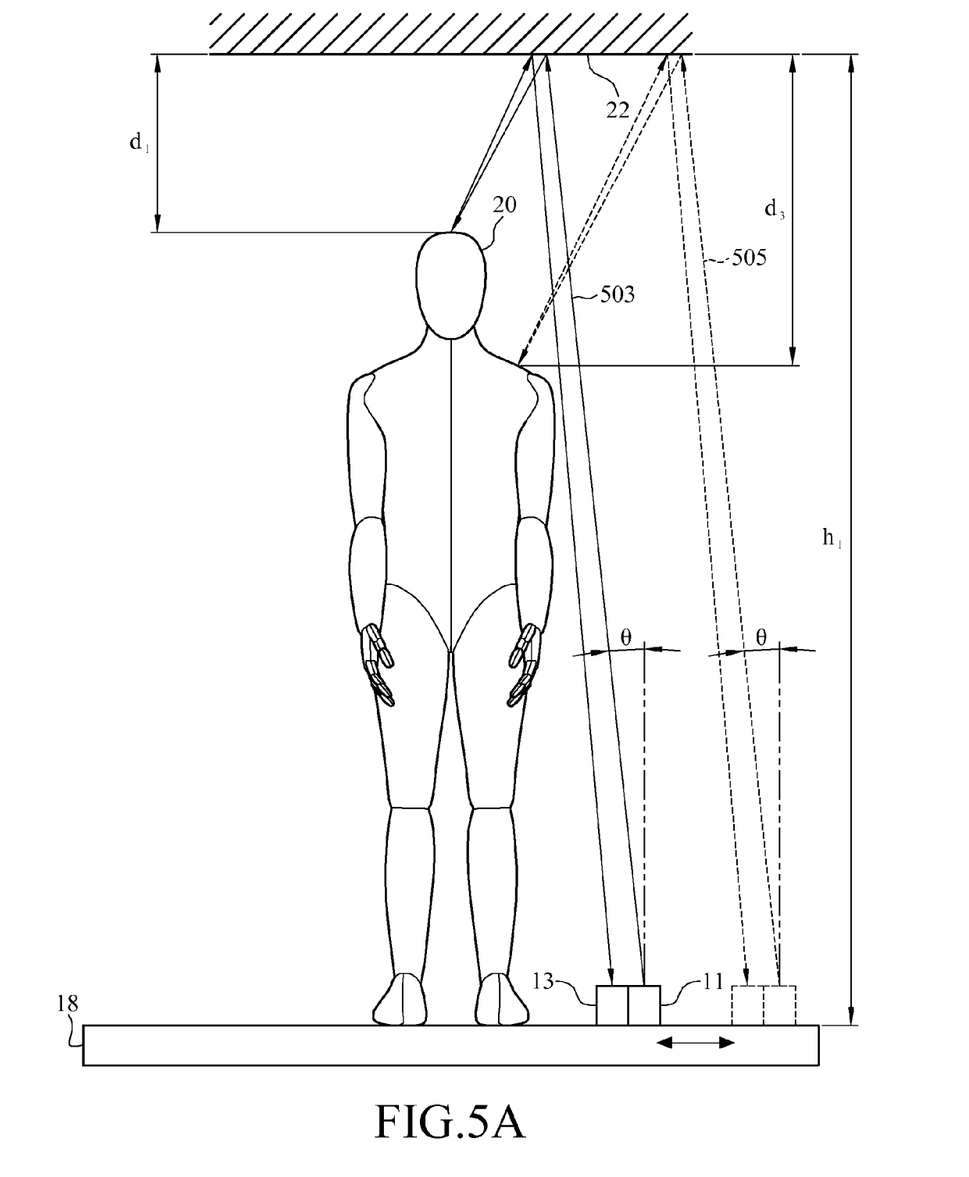
FIG. 5A illustrates a schematic view of the operation of the height measuring apparatus according to one embodiment of this invention.

As to how to accurately measure the height of the object under test, the user 24, please refer to FIG. 5A, which illustrates a schematic view of the operation of the height measuring apparatus according to one embodiment of this invention. As shown in FIG. 5A, take the height measuring apparatus in FIG. 3E for example, the first laser beam emitting module 11 firstly emits a laser beam along a first light path 503 from the first emitting position with an angle θ relative to the normal of the baseboard 18 so that a first length h1 and a second length d1 are measured. Afterwards, the first laser beam emitting module 11 adjusts the first emitting position to emit a laser beam along a second light path 505 from the adjusted first emitting position with the angle θ relative to the normal of the baseboard 18 so that the first length h1 and a third length d3 are measured. It is known that the second length d1 is shorter than the third length d3, so the control module 19 may determine that the distance between the top of the head of the user 24 and the first reflecting surface 22 is the second length d1. Then, the height of the user 24 is calculated as (h1−d1).

Figure 5B:
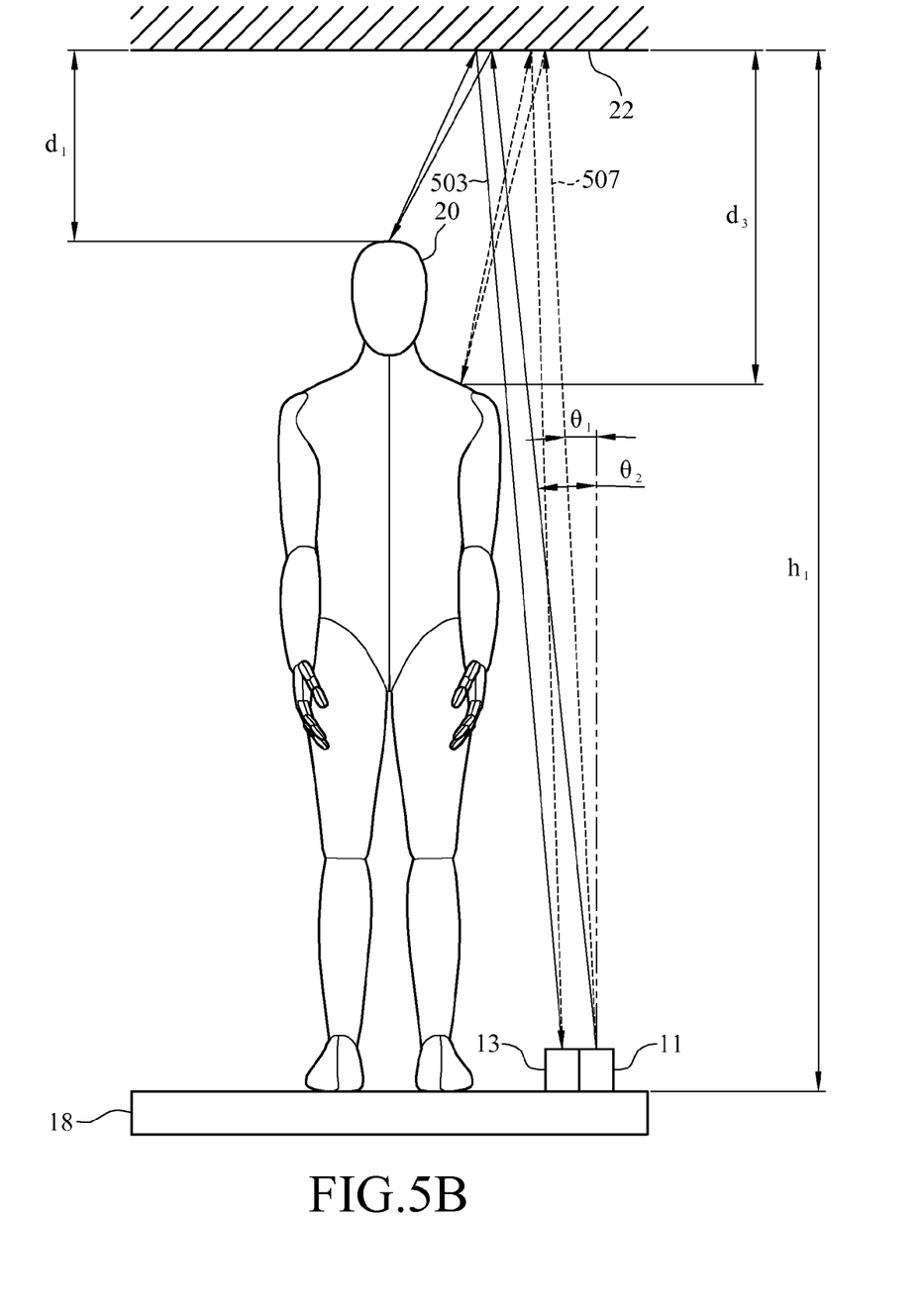
FIG. 5B illustrates one schematic view of the operation of the height measuring apparatus according to one embodiment of this invention.

In another embodiment, please refer to FIG. 5B, which illustrates one schematic view of the operation of the height measuring apparatus according to one embodiment of this invention. As shown in FIG. 5B, compared with FIG. 5A, the first laser beam emitting module 11 does not adjust the first emitting position but the first emitting angle θ. The first laser beam emitting module 11 then emits two laser beams respectively along the light path 503 with an angle θ1 relative to the normal of the baseboard 18 and along the light path 507 with an angle θ2 relative to the normal of the baseboard 18. As such, the control module 19 may obtain the first length h1, the second length d1, and the third length d3. Then, the control module 19 may determine that the distance between the top of the head of the user 24 and the first reflecting surface 22 is the second distance d1 because the second length d1 is less than the third length d3. Accordingly, the height of the user 24 is calculated to be (h1−d1).

In other words, the control module 19 may control the first laser beam emitting module 11 to emit laser beams with different light paths so as to obtain the first length d1 and a plurality of values of the second length. Then the control module 19 may select the smallest value as the second length, which is probably the distance between the top of the head of the user 24 and the first reflecting surface 22. Accordingly, the height of the user 24 may be calculated.

In one embodiment, the control module 19 may control the first laser beam emitting module 11 and the first photo detection module 13 to measure the height of the object under test for several times so as to get a plurality of height values of the object under test. Then a average value according to the plurality of height values of the object under test may be obtained to be the measured height of the object under test.

In one embodiment, when the height measuring apparatus 1 is integrated into the scale, the control module 19 may further determine to control the first laser beam emitting module 11 to emit the first laser beam and/or the second laser beam according to whether the baseboard 18 is pressed by the object under test, the user 24. For example, as shown in FIG. 3B, when the control module 19 detects and determines that the baseboard 18 is pressed by the user 24, which means that the user 24 is standing on the baseboard 18, the control module 19 will control the first laser beam emitting module 11 to emit the second laser beam to measure the summation of both of the first length h1 and the second length d1. When the user 24 has left the baseboard 18, the control module 19 may control the first laser beam emitting module 11 to vertically emit the first laser so as to measure the distance between the reflecting surface 22 and the baseboard 18, which is the first length h1. Hence, the height of the user 24, the difference between the first length h1 and the second length d1, may be calculated.

Figure 6:
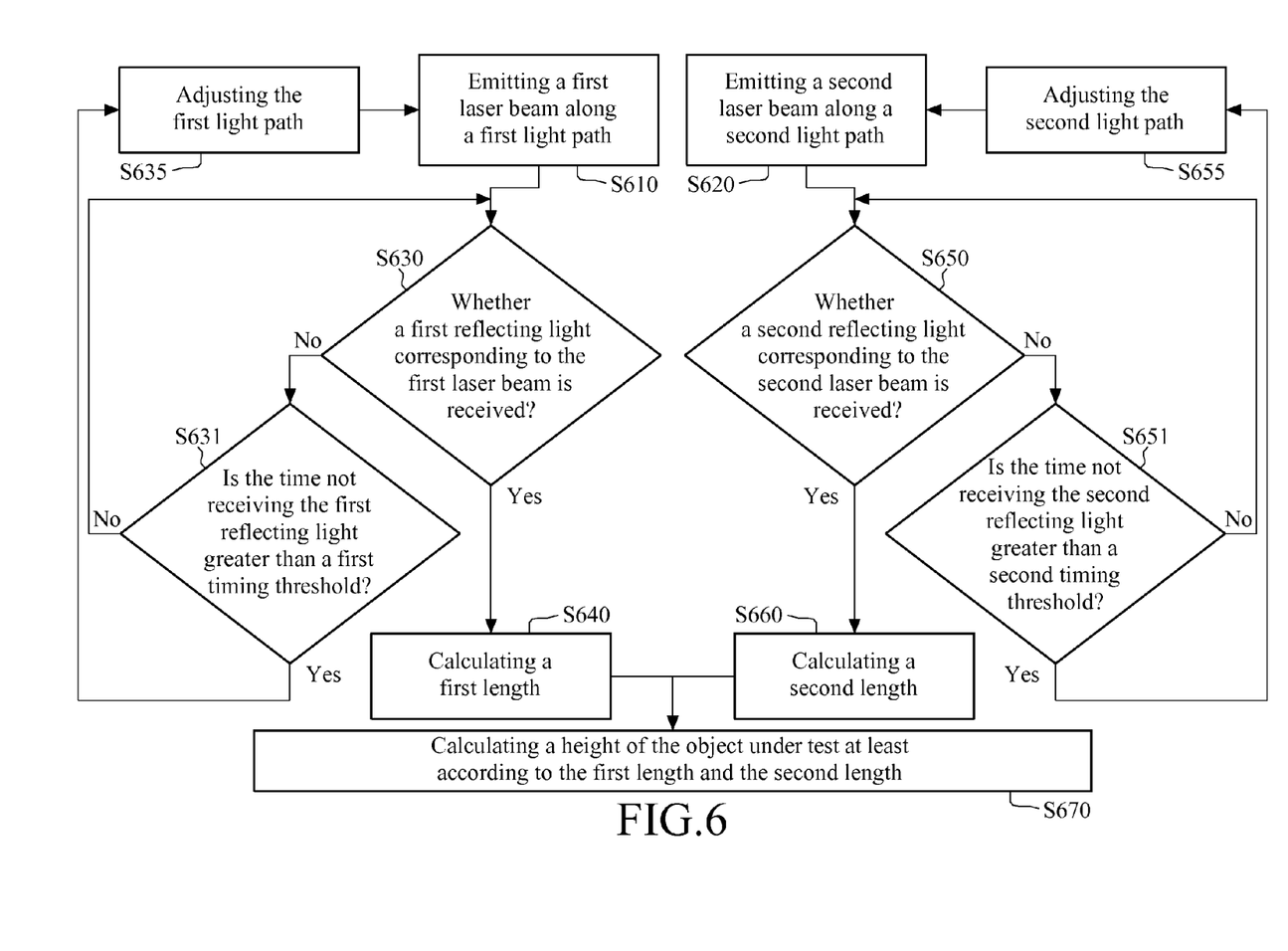
FIG. 6 is a flowchart of the height measuring method according to one embodiment of this invention.

Refer to the flow of the height measuring method, please refer to FIG. 2, FIG. 3A, FIG. 3B and FIG. 6, wherein FIG. 6 is a flowchart of the height measuring method according to one embodiment of this invention. As shown in step S610, the first laser beam emitting module 11 emits the first laser beam to the first reflecting surface, e.g., reflecting surface 22, along the first light path 201. As shown in step S620, the first laser beam emitting module 11 emits the second laser beam along the second light path 203 and the second laser beam is reflected by the first reflecting surface, the reflecting surface 22, to the object under test, the user 24. As shown in step S630, the first photo detection module 13 may determine whether the first reflecting light corresponding to the first laser beam is received. If the first reflecting light is not received, as shown in step S631, the first photo detection module 13 further determines whether the time not receiving the first reflecting light is greater than the first timing threshold. If affirmative, as shown in step S635, the control module 19 controls the first laser beam emitting module 11 to adjust the first light path and then the flow goes back to step S610. If the time not receiving the first reflecting light is less than the first timing threshold, the flow goes back to step S630. If the first reflecting light is received, as shown in step S640, the control module 19 calculates the first length according to the first piece of data corresponding to the first reflecting light. As shown in step S650, the control module 19 determines whether the second reflecting light corresponding to the second laser beam is received. If not, as shown in step S651, the control module 19 determines whether the time not receiving the second reflecting light is greater than the second timing threshold. If affirmative, as shown in step S655, the control module 19 controls the first laser beam emitting module 11 to adjust the second light path, and the flow goes back to step S620. Otherwise, the flow goes to step 650. If the second reflecting light is received, as shown in step S660, the control module 19 calculates the second length according to the second piece of data corresponding to the second reflecting light. Then, as shown in step S670, the control module 19 calculates the height of the object under test according to at least the first length and the second length.

According to the height measuring apparatus and the method thereof disclosed in the embodiments of this invention, the laser ranging method is used to measure the first length, the height of the ceiling, and the second length, the distance between the ceiling and the object under test. Then, the first length and the second length are both used for calculating the height of the object under test. According to the embodiments, it is obvious that the height measuring apparatus does not occupy much space, so it can be integrated into the scale and is easily to be carried and used in the environment with a ceiling.

It will be apparent to those skilled in the art that various modifications and variations can be made to the disclosed embodiments. It is intended that the specification and examples be considered as exemplary only, with a true scope of the disclosure being indicated by the following claims and their equivalents.

The invention claimed is:
1. A method for measuring height applicable for an environment with a first reflecting surface, the method comprises:
    emitting a first laser beam along a first light path from a baseboard;
    determining whether a first reflecting light resulting from the first laser beam reflected by the first reflecting surface is received, wherein the first reflecting light is reflected only once by the first reflecting surface;
    calculating a first length according to a first piece of data corresponding to the first reflecting light when the first reflecting light is received;
    emitting a second laser beam along a second light path from the baseboard;
    determining whether a second reflecting light resulting from the second laser beam reflected by both of the first reflecting surface and an object under test is received, the object under test is carried on a top surface of the baseboard;
    calculating a second length according to a second piece of data corresponding to the second reflecting light when the second reflecting light is received; and
    calculating a height of the object under test at least according to the first length and the second length;
    wherein the object under test is disposed between the first reflecting surface and the top surface of the baseboard.
2. The method according to claim 1, wherein the first reflecting surface is selected from a group composed of a ceiling, a wall, and a bezel.

3. The method according to claim 1, wherein whether the first reflecting light is received is determined according to a first intensity threshold and a first timing threshold.
4. The method according to claim 1, further comprising adjusting the first light path to emit the first laser beam again when the first reflecting light is not received.
5. The method according to claim 4, wherein the first light path is corresponding to a first emitting position and a first emitting angle, and the first light path is adjusted by adjusting at least one of the first emitting position and the first emitting angle.
6. The method according to claim 1, wherein whether the first reflecting light is received is determined according to a second intensity threshold and a second timing threshold.
7. The method according to claim 1, further comprising adjusting the second light path to emit the second laser beam again when the second reflecting light is not received.
8. The method according to claim 7, wherein the second light path is corresponding to a second emitting position and a second emitting angle, and the second light path is adjusted by adjusting at least one of the second emitting position and the second emitting angle.
9. The method according to claim 1, wherein the first piece of data comprises a first emitting time corresponding to the first laser beam and a first receiving time corresponding to the first reflecting light, and the second piece of data comprises a second emitting time corresponding to the second laser beam and a second receiving time corresponding to the second reflecting light, and the first length is calculated according to the first emitting time and the first receiving time, while the second length is calculated according to the second emitting time and the second receiving time.
10. The method according to claim 1, wherein the first piece of data comprises a first emitting phase corresponding to the first laser beam and first receiving phase corresponding to the first reflecting light, and the second piece of data comprises a second emitting phase corresponding to the second laser beam and a second receiving phase corresponding to the second reflecting light, and the first length is calculated according to the first emitting phase and the first receiving phase, while the second length is calculated according to the second emitting phase and the second receiving phase.
11. The method according to claim 1, further comprising:
    emitting a third laser beam along a third light path;
    determining whether a third reflecting light resulting from the third laser beam reflected by both of the first reflecting surface and an object under test is received; and
    calculating a third length according to a third piece of data corresponding to the third reflecting light when the third reflecting light is received;
    wherein, the height of the object under test is calculated according to the first length, the second length, and the third length.
12. A height measuring apparatus applicable for an environment with a first reflecting surface, the apparatus comprising:
    a baseboard having a top surface for carrying an object under test;
    at least one laser beam emitting module disposed in at least one emitting position on the top surface of the baseboard, wherein each laser beam emitting module is for emitting a first laser beam along a first light path and emitting a second laser beam along a second light path;
    at least one photo detection module disposed in at least one detecting position on the top surface of the baseboard, wherein each photo detection module is for selectively generating a first piece of data corresponding to a first reflecting light and a second piece of data corresponding to a second reflecting light by determining whether the first reflecting light resulting from the first laser beam reflected by the first reflecting surface and the second reflecting light resulting from the second laser beam reflected by both of the object under test and the first reflecting surface, wherein the first reflecting light is reflected only once by the first reflecting surface; and a control module electrically coupled to the laser beam emitting module and the photo detection module, wherein the control module is for calculating a first length according to the first piece of data, calculating a second length according to the second piece of data, and calculating a height of the object under test at least according to the first length and the second length;

wherein the object under test is disposed between the first reflecting surface and the top surface of the baseboard.

13. The apparatus according to claim 12, wherein the first reflecting is selected from a group of a ceiling, a wall, and a bezel.

14. The apparatus according to claim 12, wherein the photo detection module determines whether the first reflecting light is received according to a first intensity threshold.

15. The apparatus according to claim 12, wherein the control module further determines whether the first piece of data is received by the control module and controls the laser beam emitting module to adjust the first light path to emitting the first laser beam again by adjusting at least one of the emitting position and a emitting angle.

16. The apparatus according to claim 12, wherein the photo detection module determines whether the second reflecting light is received according to a second intensity threshold.

17. The apparatus according to claim 12, wherein the control module further determines whether the second piece of data is received by the control module and controls the laser beam emitting module to adjust the second light path to emitting the second laser beam again by adjusting at least one of the emitting position and a emitting angle.

18. The apparatus according to claim 12, wherein the first piece of data comprises a first emitting time corresponding to the first laser beam and a first receiving time corresponding to the first reflecting light, and the second piece of data comprises a second emitting time corresponding to the second laser beam and a second receiving time corresponding to the second reflecting light, and the first length is calculated according to the first emitting time and the first receiving time, while the second length is calculated according to the second emitting time and the second receiving time.

19. The apparatus according to claim 12, wherein the first piece of data comprises a first emitting phase corresponding to the first laser beam and a first receiving phase corresponding to the first reflecting light, and the second piece of data comprises a second emitting phase corresponding to the second laser beam and a second receiving phase corresponding to the second reflecting light, and the first length is calculated according to the first emitting phase and the first receiving phase, while the second length is calculated according to the second emitting phase and the second receiving phase.

20. The apparatus according to claim 12, wherein the at least one laser beam emitting module comprises:
   a first laser beam emitting module disposed in a first emitting position among the at least one emitting position for emitting the first laser beam; and
   a second laser beam emitting module disposed in a second emitting position among the at least one emitting position for emitting the second laser beam, wherein the second emitting position is different from the first emitting position.

21. The apparatus according to claim 12, wherein the at least one photo detection module comprises:
   a first photo detection module disposed in a first detecting position among the at least one detecting position for detecting the first reflecting light; and
   a second photo detection module disposed in a second detecting position among the at least one detecting position for detecting the second reflecting light, wherein the second detecting position is different from the first detecting position.

22. The apparatus according to claim 12, wherein the laser beam emitting module further emits a third laser beam along a third light path, and the photo detection module further selectively generates a third piece of data corresponding to a third reflecting light resulting from the third laser beam reflected by both of the first reflecting surface and the object under test by determining whether the third reflecting light is received, and the control module calculates the height of the object under test further according to a third length calculate according to the third piece of data.

* * * * *